United States Patent [19]

Roberg et al.

[11] Patent Number: 5,663,394

[45] Date of Patent: Sep. 2, 1997

[54] HIGH YIELD ALUMINOXANE SYNTHESIS PROCESS

[75] Inventors: John K. Roberg; Edward A. Burt, both of Baton Rouge, La.

[73] Assignee: Albemarle Corporation, Richmond, Va.

[21] Appl. No.: 680,087

[22] Filed: Jul. 15, 1996

[51] Int. Cl.$^6$ .................................................. C07F 5/06
[52] U.S. Cl. ............................................................ 556/179
[58] Field of Search ............................................. 556/179

[56] References Cited

U.S. PATENT DOCUMENTS

| | | | |
|---|---|---|---|
| 3,219,591 | 11/1965 | Vandenberg | 252/431 |
| 3,242,099 | 3/1966 | Manyik | 252/429 |
| 3,300,458 | 1/1967 | Manyik | 260/88.2 |
| 4,730,071 | 3/1988 | Schoenthal et al. | 556/179 |
| 4,730,072 | 3/1988 | Schoenthal et al. | 556/179 |
| 4,772,736 | 9/1988 | Edwards et al. | 556/179 |
| 4,908,463 | 3/1990 | Bottelberghe | 556/179 |
| 4,924,018 | 5/1990 | Bottelberghe | 556/179 |
| 4,937,363 | 6/1990 | Smith, Jr. et al. | 556/179 |
| 4,960,878 | 10/1990 | Crapo et al. | 556/179 |
| 4,968,827 | 11/1990 | Davis | 556/179 |
| 5,041,584 | 8/1991 | Crapo et al. | 556/179 |
| 5,041,585 | 8/1991 | Deavenport et al. | 556/179 |
| 5,086,024 | 2/1992 | Crapo et al. | 502/117 |
| 5,206,401 | 4/1993 | Deavenport et al. | 556/175 |
| 5,403,942 | 4/1995 | Becker et al. | 556/175 |
| 5,416,229 | 5/1995 | Tran et al. | 556/179 |
| 5,427,992 | 6/1995 | Graefe et al. | 502/111 |
| 5,436,212 | 7/1995 | Geerts | 556/179 X |

OTHER PUBLICATIONS

Manyik et al., A Soluble Chromium–Based Catalyst for Ethylene Trimerization and Polymerization, Journal of Catalysis, vol. 47, 1977, pp. 197–209.

*Primary Examiner*—Paul F. Shaver
*Attorney, Agent, or Firm*—Philip M. Pippenger

[57] ABSTRACT

Water, hydrocarbylaluminum such as trimethylaluminum, and organic solvent such as toluene are fed to a reactor in controlled proportions and under temperature control to form a dilute reaction product mixture of specified composition and concentration. This solution is then processed so as to form at least two product mixtures, one of which is essentially aluminoxane-free hydrocarbylaluminum dissolved in organic solvent, and another of which is a concentrated solution of organoaluminum compounds composed in essence of hydrocarbylaluminum (e.g. trimethylaluminum) and hydrocarbylaluminoxane (e.g., methylaluminoxane) in organic solvent in which the amount aluminoxane far exceeds the amount of hydrocarbylaluminum. The process fulfills the need for practical, commercially-feasible process technology capable of producing concentrated aluminoxane solutions with no significant yield losses, and by process technology that can be applied both to batch and to continuous modes of operation.

27 Claims, 5 Drawing Sheets

HIGH YIELD ALUMINOXANE SYNTHESIS PROCESS

TECHNICAL FIELD

This invention relates to the production of alkylaluminoxanes by use of a novel cost-effective process which makes it possible to operate with no significant yield losses.

BACKGROUND

Aluminoxanes are of commercial importance as components used in forming polymerization and oligomerization catalysts. They are formed by controlled hydrolysis of aluminum alkyls such as trimethylaluminum. While the hydrolysis can be effected by use of hydrated crystalline salts such as the pentahydrate of copper sulfate or the like, this approach can lead to the presence in the product of small amounts of metal residues which can act as catalyst poisons. Thus the use of water itself to effect controlled hydrolysis of the aluminum alkyl in a hydrocarbon medium has proven to be the preferred general approach.

Over the years considerable effort has been devoted to processes for conducting such controlled hydrolysis using water as the hydrolytic reagent. For example, Vandenberg, U.S. Pat. No. 3,219,591 reported the catalytic activity of compounds formed by the reaction of trialkylaluminum with limited amounts of water in the polymerization of epichlorohydrin and other oxiranes. Shortly thereafter, Manyik, et al. U.S. Pat. No. 3,242,099 reported the use of aluminoxanes, made by reacting 0.85–1.05 moles of water with hydrocarbylaluminum compounds such as triisobutylaluminum, as co-catalysts with certain transition metal compounds in the polymerization of mono-unsaturated alpha-olefins; e.g. ethylene and propylene. Isobutylaluminoxane was also made by adding an equal mole quantity of water to a heptane solution of triisobutylaluminum.

Manyik, et al. U.S. Pat. No. 3,300,458 describe preparing alkylaluminoxane by passing a hydrocarbon through water to form a wet hydrocarbon and mixing the wet hydrocarbon and an alkyl aluminum/hydrocarbon solution in a conduit. Manyik, et al. in *Journal of Catalysis* Volume 47 published in 1977, at pages 197–209, refer to studies with catalysts formed from certain chromium compounds and partially hydrolyzed triisobutylaluminum.

Schoenthal, et al. U.S. Pat. No. 4,730,071 shows the preparation of methylaluminoxane by dispersing water in toluene using an ultrasonic bath to cause the dispersion and then adding a toluene solution of trimethylalaminum to the dispersion. Schoenthal, et al. U.S. Pat. No. 4,730,072 is similar except it uses a high speed, high shear-inducing impeller to form the water dispersion.

Edwards, et al. U.S. Pat. No. 4,772,736 describes an aluminoxane preparation process in which water is introduced below the surface of a solution of hydrocarbylaluminum adjacent to a stirrer which serves to immediately disperse the water in the hydrocarbon solution.

Bottelberghe U.S. Pat. No. 4,908,463 describes an aluminoxane preparation process in which a static mixer is used to disperse water in a solvents and then impinges the water dispersion with a hydrocarbylaluminum solution in a T-shaped reactor. The solution is then removed to a finished reaction vessel which is stirred and can have a cooling means such as a heat-exchanger in an external pump-around loop.

Bottelberghe U.S. Pat. No. 4,924,018 describes formation of aluminoxanes by feeding a hydrocarbon solution of aluminum alkyl to a reaction zone, feeding an emulsion of 0.5–10 weight percent water in an inert solvent to the reaction zone, the ratio of moles of water to aluminum atoms being about 0.4–1:1, and removing reaction mixture from the reaction zone to maintain a constant liquid level therein. The feeds are controlled so that the average residence time in the reaction zone is no more than about one hour.

Smith, Jr., et al. U.S. Pat. No. 4,937,363 discloses forming aluminoxanes by forming in a column a thin falling film of a solution of aluminum alkyl in an inert solvent while passing an upward countercurrent flow of wet inert gas through the column.

Davis U.S. Pat. No. 4,968,827 teaches introducing water into the free space above the surface of a cold (−80° C. up to −10° C.) solution of hydrocarbylaluminum compound in a liquid hydrocarbon which is being intensively agitated.

Deavenport, et al. U.S. Pat. No. 5,041,585 and 5,206,401 teach preparation of aluminoxanes by contacting an organic solvent containing trialkylaluminum with atomized water. Preformed aluminoxane can be included in the solution as reaction moderator.

Becker et al. U.S. Pat. No. 5,403,942 and Graefe et al. U.S. Pat. No. 5,427,992 describe batch processes for preparing aluminoxanes by injecting water into trialkylaluminum solutions using respectively, a jet loop reactor and a rotor/stator machine to mix the water and trialkylaluminum.

U.S. Pat. No. 4,960,878; 5,041,584 and 5,086,024 also describe processes in which water and certain organoaluminum compounds are caused to interact.

Despite all such intensive study and research, a need exists for practical, commercially-feasible process technology capable of producing concentrated aluminoxane solutions with no significant yield losses, especially where such technology can be applied both to batch and to continuous modes of operation.

This invention is deemed to fulfill the foregoing need in a highly efficient manner.

SUMMARY OF THE INVENTION

The present invention is applicable to, and constitutes an improvement in, processes wherein water, hydrocarbylaluminum, and organic solvent are used in forming hydrocarbylaluminoxane. In accordance with this invention the feeds of these materials to the reactor are controlled to form a dilute reaction product mixture which is then processed so as to form at least two product mixtures, one of which consists essentially of hydrocarbylaluminum dissolved in organic solvent, and another of which is a concentrated solution of organoaluminum compounds (i.e., a mixture consisting essentially of hydrocarbylaluminum and hydrocarbylaluminoxane) in organic solvent in which the amount aluminoxane far exceeds the amount of hydrocarbylaluminum therein. As used herein, the term "hydrocarbylaluminum" is distinct from and does not include "aluminoxane" or "hydrocarbylaluminoxane".

In accordance with one embodiment of this invention the improvement comprises (a) feeding hydrocarbylaluminum, an organic solvent, and water to a reactor under temperature conditions and in proportions that form a solution containing in the range of about 0.5 to about 15 wt % of aluminum as hydrocarbylaluminum and hydrocarbylaluminoxane, and wherein for each mole part of aluminum in the solution, there is in the solution in the range of about 0.1 to about 0.9 mole part of hydrocarbylaluminum; and (b) separating the solution into a first portion consisting essentially of about 0.5 to about 15 wt % of aluminum as hydrocarbylaluminum dissolved in organic solvent, and a second portion consisting essentially of about 3 to about 20 wt % of total aluminum as hydrocarbylaluminum and hydrocarbylaluminoxane, and wherein for each mole part of aluminum in solution in said second portion, there is in the range of only about 0.03 to about 0.3 mole part of hydrocarbylaluminum. Substantially the entire balance of dissolved aluminum in the second portion is composed of hydrocarbylaluminoxane. In preferred embodiments, the first portion is recycled to the reactor.

In particularly preferred embodiments, the process is conducted on a continuous basis, particularly in operations wherein the first portion is continuously recycled to the reactor. In conducting the process on a continuous basis it is highly desirable, though not essential, to perform the reaction in a continuous loop reactor or pump-around system such as described in commonly-owned copending U.S application Ser. No. 09/635,310, filed Apr. 19, 1996, now U.S. Pat. No. 5,599,964, issued Feb. 4, 1997. It is also advantageous, though not essential, to utilize the modes of water feed or injection described in commonly-owned copending U.S. applications Ser. No. 08/635,358, and Ser. No. 08/635,310, both filed Apr. 19, 1996. The entire disclosures of these applications are incorporated herein by reference as if fully set forth herein.

These and other embodiments of the invention will be still further apparent from the ensuing description and appended claims.

FURTHER DESCRIPTION OF THE INVENTION

Figure 1:
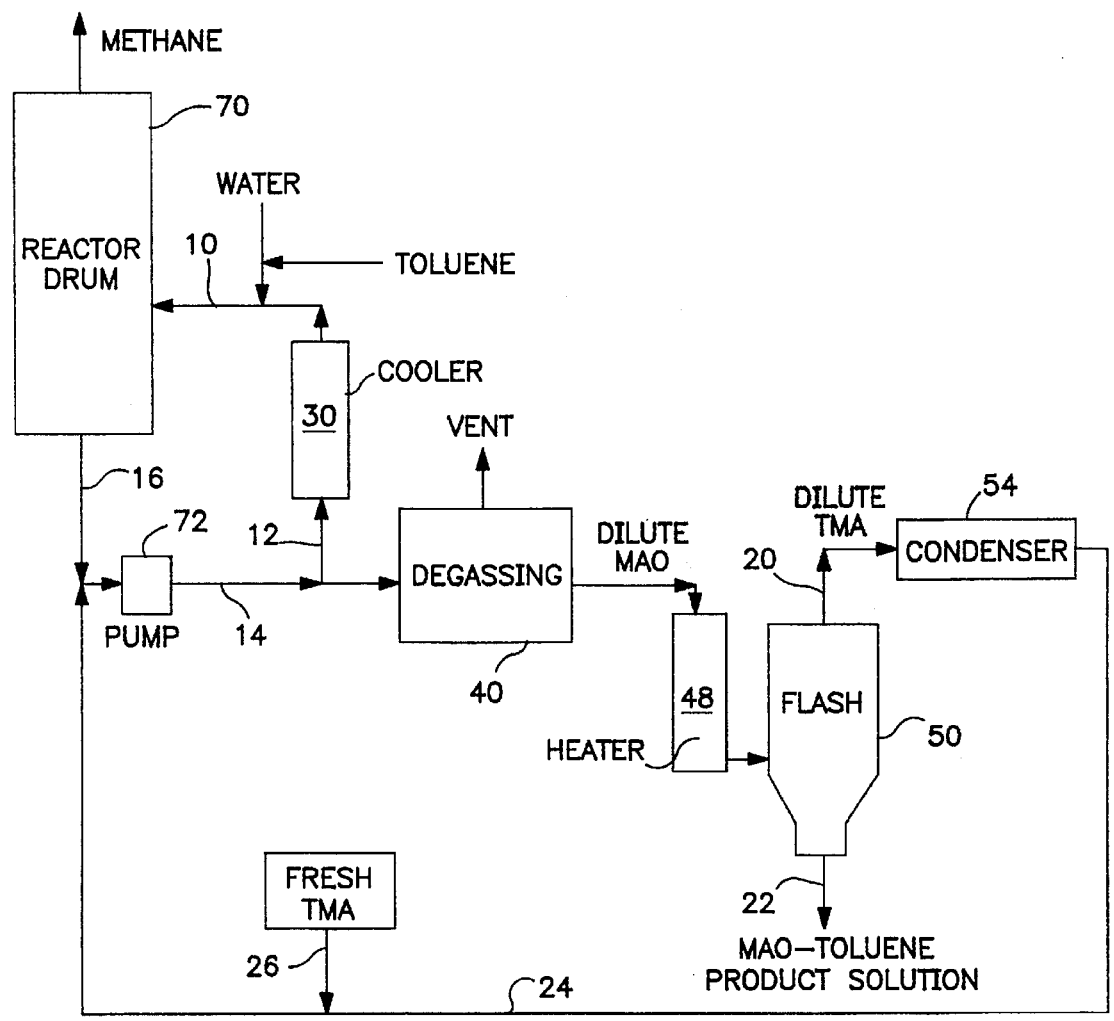
FIGS. 1 through 5 are various schematic process flow diagrams of plant facilities that can be used in the practice of this invention. In these drawings like numerals represent like components among the several views. These drawings are presented for purposes of illustration, and thus are simplified in the sense that valves, motors, holdup tanks, filters, additional pumps, etc., are not depicted therein. Such details are unnecessary for an understanding of this invention and can be provided as desired in accordance with well-established chemical engineering principles. unnecessary for an understanding of this invention and can be provided as desired in accordance with well-established chemical engineering principles.

Hydrocarbylaluminoxanes may exist in the form of linear, cyclic, caged or polymeric structures with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts are oligomers, and these usually contain about 4 to 20 of the repeating units:

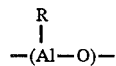

where R is $C_1$–$C_8$ alkyl and is preferably methyl. The exact structure of aluminoxanes has not been defined and they may contain linear, cyclic, caged and/or cross-linked species. Methylaluminoxanes (MAOs) normally have lower solubility in organic solvents than higher alkylaluminoxanes and the methylaluminoxane solutions tend to be cloudy or gelatinous due to the separation of particles and agglomerates. In order to improve the solubility of the methylaluminoxane, higher alkyl groups, e.g. $C_2$ to $C_{20}$ can be included such as by hydrolyzing a mixture of trimethylaluminum with up to 50 mole percent of a $C_2$ to $C_{20}$ alkylaluminum compound such as, for example, triethylaluminum, tri-n-propylaluminum, triisobutylaluminum, tri-n-hexylaluminum, tri-n-octylaluminum or a triarylaluminum. The MAO's can also contain up to about 20 mole percent, based on aluminum, of moieties derived from amines, alcohols, ethers, esters, phosphoric and carboxylic acids, thiols, alkyl and aryl disiloxanes and the like to further improve activity, solubility and/or stability. Except as the context otherwise indicates by virtue of the specific materials specified for use (e.g., in the Examples hereinafter), such modified and mixed methyl-higher alkyl or aryl aluminoxanes are included in the term "methylaluminoxane" as used herein.

Any hydrocarbylaluminum compound or mixture of compounds capable of reacting with water to form an aluminoxane can be used. This includes, for example, trialkylalumminum, trialkenylaluminum, triarylalumminum, tricycloalkylalumminum, triaralkylaluminum, mixed alkyl arylaluminum, dialkylaluminum hydride and the like.

Preferred hydrocarbylaluminum compounds are the alkylaluminum compounds, especially trialkylaluminum compounds such as trimethylaluminum, triethylaluminum, triisobutylaluminum, tri-n-hexylaluminum, trioctylaluminum, and the like. Of these, the more preferred are the tri-$C_{1-4}$-alkylaluminum compounds.

It will be appreciated that when the separated solution consisting essentially of hydrocarbylaluminum compound (s) and solvent is recycled, small amounts of aluminoxane may also be recycled therewith, although the less, the better. The process of the invention thus includes not only the addition of water to hydrocarbylaluminum compounds, but to mixtures of aluminoxanes and hydrocarbylaluminum compounds as well.

The reaction is carried out in an inert solvent. Any inert solvent can be used. The preferred solvents are aliphatic and aromatic hydrocarbons. Aromatic hydrocarbons are more preferred. Examples include toluene, xylene, ethylbenzene, cumene, mesitylene and the like. The most preferred solvent is toluene.

The water can be added to the reaction either neat and/or dissolved or dispersed in the solvent. The reactants are combined in proportions to provide from about 0.5 to 8.0 moles of hydrocarbylaluminum compound per mole of water. When making methylaluminoxanes, the proportions are preferably from about 1.3 to 6.0 moles of trimethylaluminum and more preferably from about 2.0 to about 5.0 moles per mole of water.

Suitable reaction temperatures fall in the range of from about $-70°$ to $100°$ C., with a preferred range being about $-50°$ to $50°$ C. A more preferred range is from about $-20°$ to $20°$ C.

The following examples illustrate preferred procedures for conducting the process of this invention. All percentages given in these examples are by weight, and are approximate as they are largely based on computer simulations from bench scale studies. It is to be clearly understood that these examples are for the purposes of illustrating current best modes contemplated for carrying out the operations. They are not intended to limit, and should not be construed as limiting, the invention to the specific details set forth therein.

EXAMPLE 1

To a continuous loop reactor system such as depicted in FIG. 1 hereof composed in essence of reactor 70, pump 72, cooler 30, and lines 10, 12, 14 and 16 (see also commonly-owned copending U.S. application Ser. No. 09/635,310, filed Apr. 19, 1996), are continuously charged via line 10, 718 kg/hr of 3.8 wt % of trimethylaluminum (TMA) in toluene, 13 kg/hr of toluene and 1.36 kg/hr of water. This provides a ratio of water to aluminum of 0.2. The reaction mixture is maintained at a temperature of about 2° C. by circulation through cooler 30. The reaction product after degassing in degasser 40 is approximately 730 kg/hr of 96.3 wt % toluene, 3.0 wt % TMA, 0.7 wt % methylaluminoxane (MAO). With a 10 micron filter in the system (not shown), virtually no solids are detected, and thus under these reaction conditions, no aluminum is lost as solids. Continuous flash in still unit 50 operated at 105 mmHg and 55° C. gives a separation into (a) an overhead or take-off in line 20 at the rate of about 712 kg/hr of a solution of approximately 3.0 wt % TMA and 97 wt % toluene, and (b) bottoms in line 22 at the rate of approximately 18 kg/hr of a product solution composed of about 27% MAO, 3% TMA, and 70% toluene. Heater 48 raises the temperature of the feed to unit 50 and thus supplies the heat used in the operation of unit 50. Addition via line 26 of 6 kg/hr of 100% TMA to the condensed overhead in line 24 regenerates the TMA feed rate, which is recycled to the loop reactor system.

EXAMPLE 2

Figure 2:
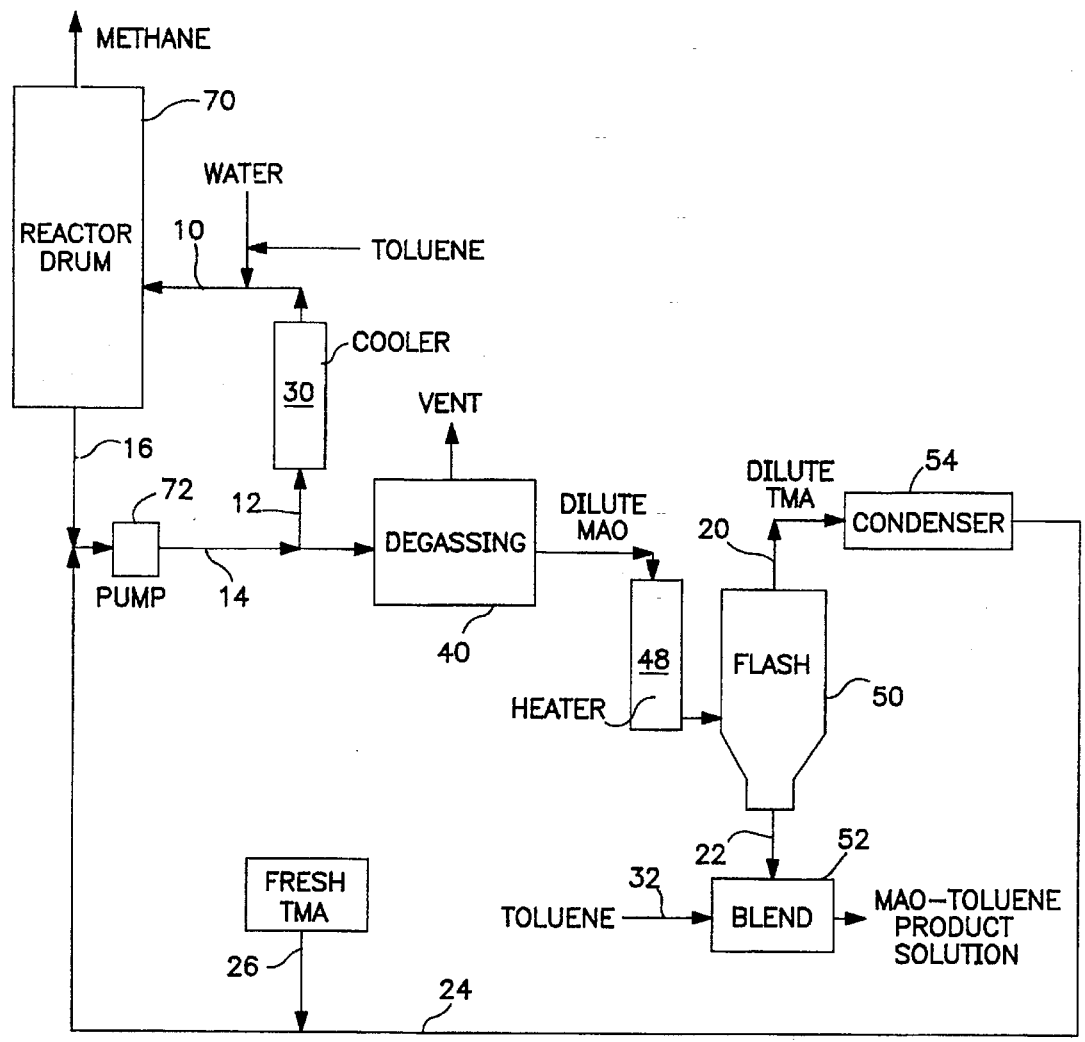

In this case the flow scheme as depicted in FIG. 2 is used. This is essentially the same arrangement as in FIG. 1 except that the bottoms in line 22 are directed to blending tank 52 to enable adjustment of concentration through dilution with additional solvent. Thus in this case there are continuously charged to the reactor 70, 454.5 kg/hr of 6.0 wt % TMA in toluene, 8.4 kg/hr of toluene and 1.36 kg/hr of water. This provides a ratio of water to aluminum of 0.2. The reaction mixture in the continuous loop reactor system is maintained at a temperature of about 2° C. The reaction product after degassing in degasser 40 is approximately 462 kg/hr of 94% toluene, 5% TMA, and 1% MAO. With a 10 micron filter in the system (not shown), virtually no solids are detected. Thus under these reaction conditions, no aluminum is lost as solids. Continuous flash in unit 50 operated at 105 mmHg and 55° C. gives a separation into (a) an overhead or take-off in line 20 at the rate of approximately 448.5 kg/hr of a mixture of about 4.7% TMA and 95.3% toluene, and (b) bottoms in line 22 at the rate of approximately 13.5 kg/hr of a solution of about 35.8% MAO, 4.5% TMA, and 59.7% toluene. The overhead is liquefied in condenser 54 and recycled to the loop reactor system or section composed of reactor 70, pump 72, cooler 30, and lines 10, 12, 14 and 16, all as in Example 1. Addition via line 32 of approximately 4.3 kg/hr of toluene to the bottoms in tank 52 gives approximately 18 kg/hr of a desired product concentrate composed of about 27% MAO, 3% TMA, and 70% toluene. Addition via line 26 of 6 kg/hr of 100% TMA to the condensed overhead in line 24 regenerates the TMA feed rate, which is recycled to the loop reactor system.

EXAMPLE 3

Figure 3:
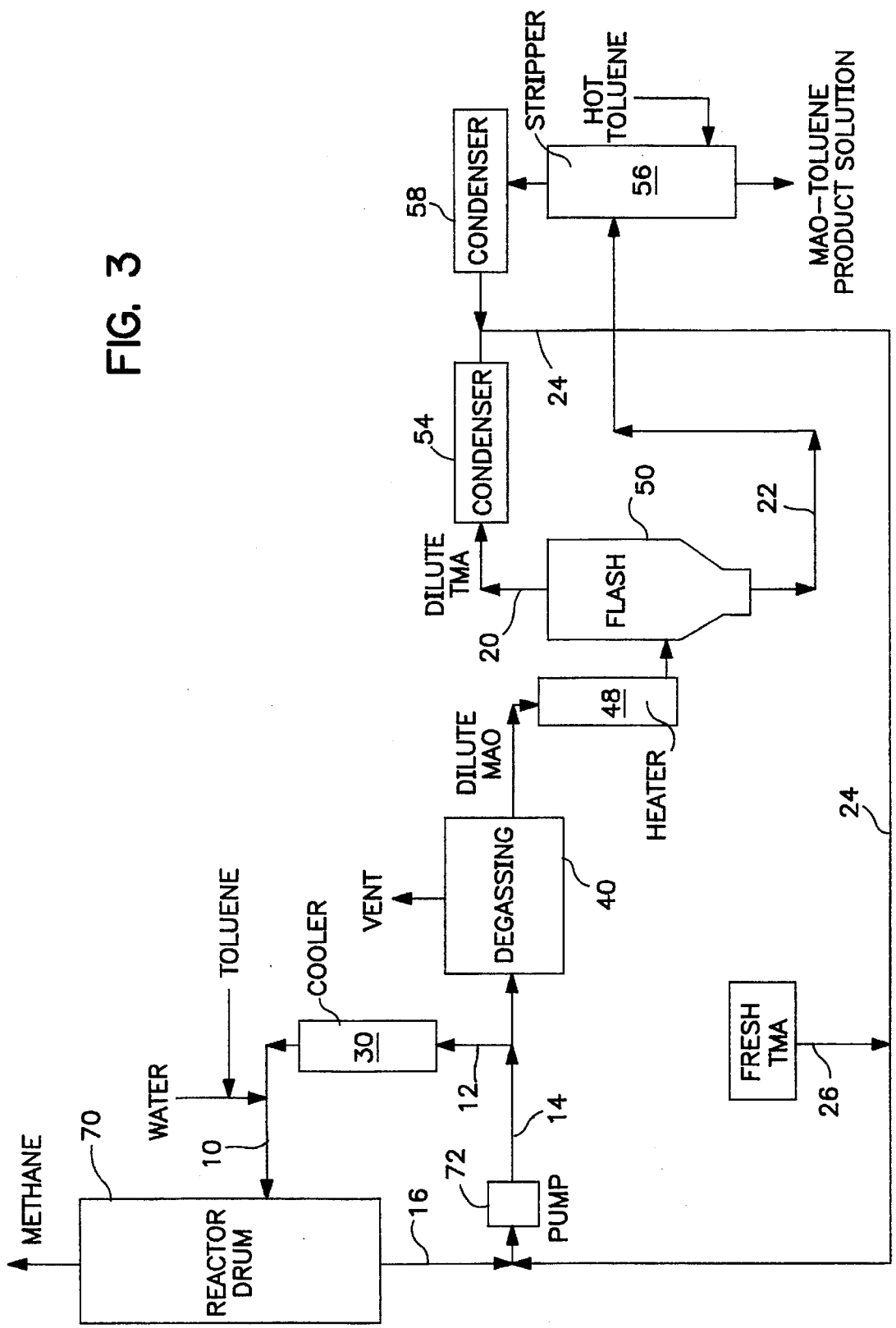

The system depicted in FIG. 3 is used in this example. The only difference between the systems of FIGS. 1 and 3 resides in the product workup portion of the operation. Thus to the continuous loop reactor are continuously charged 419.5 kg/hr of 6.5 wt % TMA in toluene, 4.5 kg/hr of toluene and 1.36 kg/hr of water. This provides a ratio of water to aluminum of 0.2. The reaction mixture is maintained at a temperature of about 2° C. The reaction product after degassing is approximately 423.5 kg/hr of a mixture composed of about 94% toluene, 5% TMA, and 1% MAO. With a 10 micron filter (not shown) in the system, virtually no solids are detected. Thus under these reaction conditions, no aluminum is lost as solids. Continuous flash at 105 mmHg and 55° C. gives a separation into (a) an overhead or take-off in line 20 at the rate of approximately 404 kg/hr of a solution composed of about 5.1% TMA and 94.9% toluene, and (b) bottoms in line 22 at the rate of about 19.3 kg/hr of a mixture containing about 69.3% toluene, 5.7% TMA and 25% MAO. The bottoms stream is transferred to a 10-stage stripper column 56, where it is introduced at the top, and 8.2 kg/hr of toluene vapor at 110° C. is introduced at the bottom. The resulting overhead is approximately 9.6 kg/hr of a solution of approximately 5.1% TMA and 94.9% toluene. The two overhead streams after liquefaction in respective condensers 54 and 58 are merged into line 24 and combined with 6 kg/hr of 100% TMA from line 26 to regenerate the TMA feed rate, which is recycled to the loop reactor section. The stripper bottoms product is a concentrate of approximately 27% MAO, 3% TMA and 70% toluene obtained at the rate of about 18 kg/hr.

EXAMPLE 4

Figure 4:
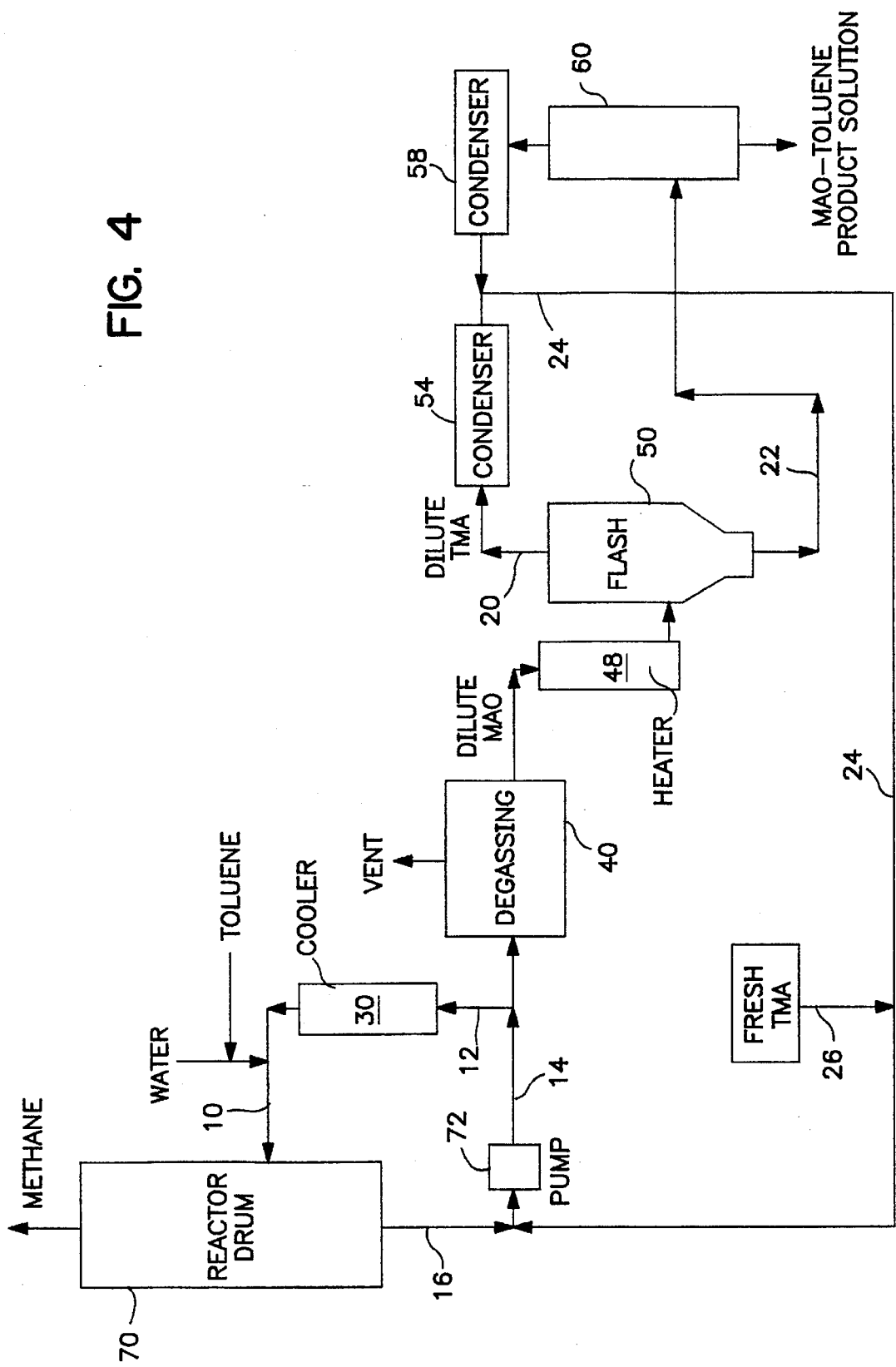

Used is the system of FIG. 4 which includes a loop reactor arrangement as in Examples 1–3 above and a wiped fill evaporator 60. Except for use of wiped film evaporator 60 instead of stripper column 56, the systems of FIGS. 3 and 4 are essentially the same. The continuous feeds to the reactor 70 are 718 kg/hr of 3.8 wt % TMA solution, 135 kg/hr of toluene and 1.36 kg/hr of water, which equates to a ratio of water to aluminum of 0.2. The reaction mixture is maintained at a temperature of about 2° C. The reaction product after degassing in unit 40 is approximately 730 kg/hr of a mixture composed of about 96.3 wt % toluene, 3.0 wt % TMA and 0.7 wt % MAO. With a 10 micron filter in the system, virtually no solids are detected. Thus under these reaction conditions, no aluminum is lost as solids. Continuous flash in unit 50 operated at 210 mmHg and 72° C. gives a separation into (a) an overhead or take-off in line 20 at the rate of about 690 kg/hr of a solution composed od approximately 2.95 wt % TMA and 97.05 wt % toluene, and (b) bottoms in line 22 at the rate of about 40 kg/hr of approximate composition 12.2% MAO, 3.8% TMA and 84% toluene. The bottoms are continuously fed to the wiped film evaporator 60 operated at 105 mmHg and 55° C. which gives as overhead, about 22 kg/hr of a solution composed of approximately 3.7 wt % TMA and 96.3 wt % toluene, and as bottoms at the rate of about 18 kg/hr, a solution composed of about of 27% MAO, 4% TMA and 69% toluene. The two overhead streams after liquefaction in respective condensers 54 and 58 are merged and combined with 6 kg/hr of 100% TMA from line 26 to regenerate the proper TMA feed composition and rate, which composition is recycled to the loop reactor section.

EXAMPLE 5

To the continuous loop reactor section of a system such as depicted in FIG. 1 hereof are continuously charged via line 10, 614 kg/hr of 4.3 wt % of trimethylaluminum (TMA) in toluene, 10 kg/hr of toluene and 1.36 kg/hr of water. This provides a ratio of water to aluminum of 0.2. The reaction mixture in the loop reactor section is maintained at a temperature of about 2° C. by circulation through cooler 30. The reaction product after degassing in degasser 40 is approximately 624 kg/hr of a mixture of approximate composition 95.7 wt % toluene, 3.4 wt % TMA, 0.8 wt % methylaluminoxane (MAO). With a 10 micron filter in the system (not shown), very little solids are detected, and thus under these reaction conditions, essentially no aluminum is lost as solids. Continuous flash in still unit 50 operated at 105 mmHg and 55° C. gives a separation into (a) an overhead or take-off in line 20 at the rate of about 606 kg/hr of a solution of approximately 3.3 wt % TMA in toluene, and (b) bottoms in line 22 at the rate of approximately 18 kg/hr of a product solution composed of about 27% MAO, 3% TMA, and 70% toluene. Addition via line 26 of 8 kg/hr of 80% TMA in toluene to the condensed overhead in line 24 regenerates the TMA feed, which is recycled to the loop reactor system.

Example 6 illustrates a modification wherein less stringent process control is used in order to achieve process economies. In this embodiment, small losses in yield based on aluminum used are accepted and effectively dealt with, all in return for improved overall economies of plant operation.

EXAMPLE 6

Figure 5:
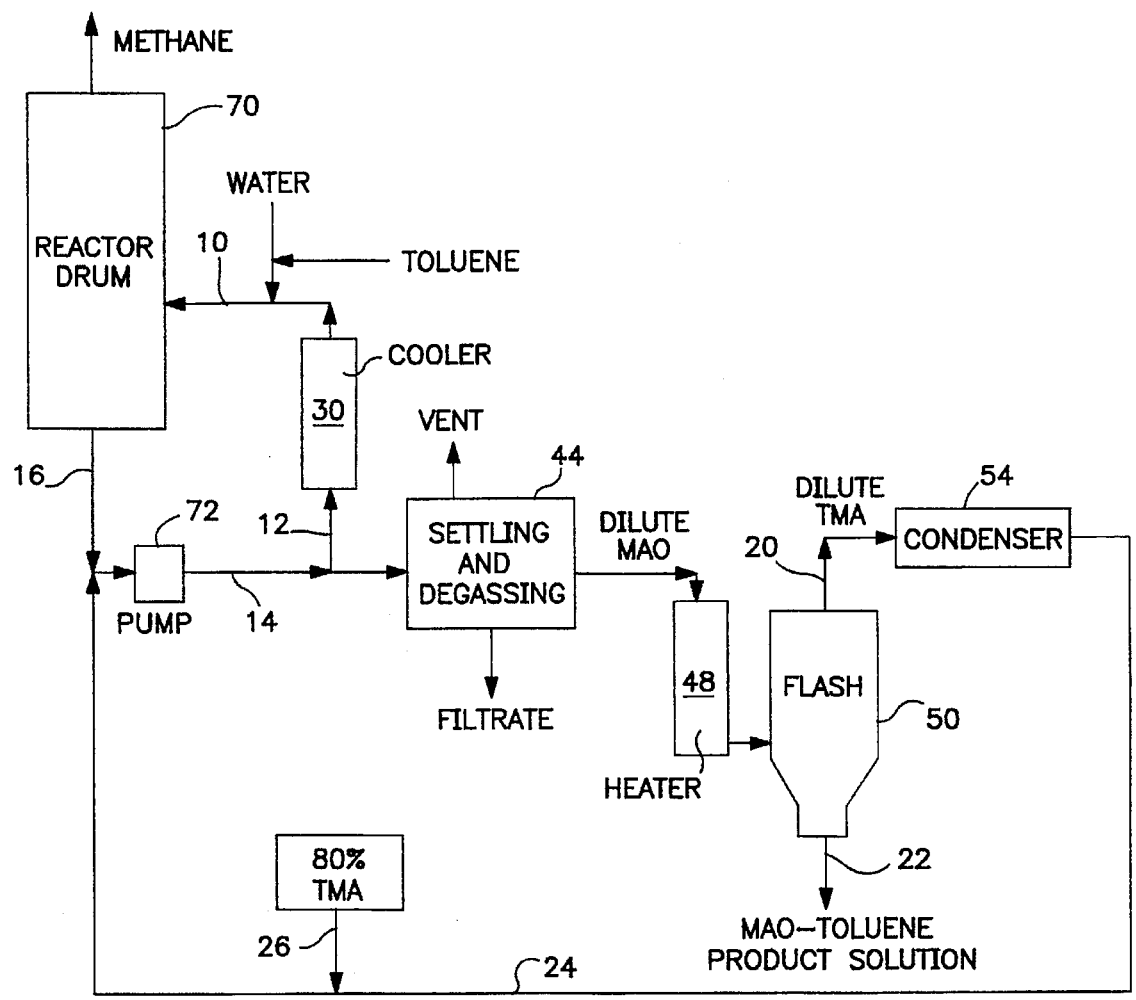

The overall system used is as schematically depicted in FIG. 5. It will be seen that this system is basically the same as that of FIG. 1 except that degasser unit 40 of FIG. 1 is replaced by settling and degasser unit 44. Unit 44 is designed to both de-gas the reaction product from the continuous loop reactor section and to cause solids in the reaction product to settle and be filtered from the liquid phase before the liquid reaction product is partitioned in unit 50. Thus, to the continuous loop reactor section comprising reactor 70, pump 72, cooler 30 and lines 10, 12, 14 and 16 are continuously charged via line 10, 364 kg/hr of 5.0 wt % of trimethylaluminum (TMA) in toluene, 22 kg/hr of toluene and 1.36 kg/hr of water, which corresponds to a ratio of water to aluminum of 0.3. The reaction mixture in the loop reactor section is maintained at a temperature of about 2° C. by circulation through cooler 30. The reaction product after degassing and solids removal in unit 44 is approximately 374 kg/hr of a mixture of approximate composition 95.3 wt % toluene, 3.3 wt % TMA, 1.3 wt % methylaluminoxane (MAO). With a 10 micron filter in unit 44, a loss of about 3 mole % of total aluminum is incurred. Continuous flash in still unit 50 operated at 105 mmHg and 55° C. gives a separation into (a) an overhead or take-off in line 20 at the rate of about 356 kg/hr of a solution of approximately 3.3 wt % TMA in toluene, and (b) bottoms in line 22 at the rate of approximately 18 kg/hr of a product solution composed of about 27% MAO, 3% TMA, and 70% toluene. Addition via line 26 of 8 kg/hr of a solution of 80 wt % TMA in toluene to the condensed overhead in line 24 regenerates the TMA feed, which is recycled to the loop reactor section.

When operating with solids formation as in Example 6, the solution from the reactor section should contain a limited amount of finely-divided aluminum-containing solids. In general, the total amount of aluminum in the solids should be not more than about 10% of the total weight of all aluminum species present (i.e., in solution and in the solids). These finely divided solids, will typically have particle sizes in a range that will pass through a 50 micron filter but will be retained by a 10 micron filter.

In preferred embodiments, this invention thus provides a continuous process of forming methylaluminoxane. The process involves in stage (a), continuously feeding trimethylaluminum, water, and organic solvent to a reactor under temperature conditions and in proportions that form a solution containing a total in the range of about 0.5 to about 8 wt % of aluminum as trimethylaluminum and methylaluminoxane, and wherein for each mole part aluminum in the solution, the solution contains in the range of about 0.10 to about 0.63 (most preferably in the range of about 0.16 to about 0.63) mole parts of trimethylaluminum. In stage (b) the reaction solution formed in (a) is continuously degassed. Then in stage (c), the degassed solution is continuously flashed to form an overhead which is essentially about 0.5 to about 8 wt % of aluminum as trimethylaluminum dissolved in organic solvent, and bottoms composed essentially of about 4 to about 20 wt % of aluminum as methylaluminoxane and trimethylaluminum. For each mole part of aluminum in solution in these bottoms, there is in the range of no more than about 0.03 to about 0.3 (most preferably in the range of about 0.05 to about 0.20) mole part of trimethylaluminum. Stage (d) involves recycling as a portion of the feed in stage (a), at least a portion of the overhead of stage (c). For such continuous operation, makeup trimethylaluminum and makeup inert solvent are included in the feed in stage (a), and most preferably trimethylaluminum and inert solvent of the feed of stage (a) are composed or made up of (i) the recycle from stage (d), (ii) the makeup trimethylaluminum, and (iii) the makeup inert solvent. In this way, the proportions of (a) are maintained by this feed. As indicated in the Drawings, it is desirable to combine the makeup trimethylaluminum (and more preferably also a portion of the makeup inert solvent) with the recycle from stage (d) before the feed in stage (a). Likewise, it is most preferred to mix together the water and a portion of the inert solvent of the feed of stage (a) before these are fed in stage (a). For this purpose the use of the modes of water feed or injection described in commonly-owned copending U.S. applications Ser. No. 09/635,358, and Ser. No. 09/635,310, referred to above, are particularly advantageous. A particularly preferred way of effecting the feeds in stage (a) comprises combining the makeup trimethylaluminum and a portion of the makeup inert solvent with the recycle from stage (d) and feeding this combined mixture in stage (a), and in addition, combining the water and another makeup portion of inert solvent and feeding this combined mixture in stage (a).

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

Unless otherwise expressly stated, all boiling temperatures set forth in this disclosure and in the claims hereof are specified at atmospheric pressure.

Each and every patent or other publication referred to in any portion of this specification is incorporated in toto into this disclosure by reference for all purposes, as if fully set forth herein. Likewise, the entire disclosures of the two copending patent applications identified and referred to herein are fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. In a process wherein hydrocarbylaluminum, water, and organic solvent are fed to a reactor to form hydrocarbylaluminoxane, the improvement which comprises (a) feeding such materials to the reactor under temperature conditions and in proportions that form a solution containing in the range of about 0.5 to about 15 wt % of aluminum as hydrocarbylaluminum and hydrocarbylaluminoxane, and wherein for each mole part of aluminum in the solution, there is in the solution in the range of about 0.1 to about 0.9 mole part of hydrocarbylaluminum; and (b) separating the solution into a first portion consisting essentially of about 0.5 to about 15 wt % of aluminum as hydrocarbylaluminum dissolved in organic solvent, and a second portion consisting essentially of about 3 to about 20 wt % of total aluminum as hydrocarbylaluminoxane and hydrocarbylaluminum, and wherein for each mole part of aluminum in solution in said second portion, there is in the range of no more than about 0.03 to about 0.3 mole part of hydrocarbylaluminum.

2. A process according to claim 1 which further comprises recycling at least part of said first portion to the reactor.

3. A process according to claim 1 wherein (a) and (b) are conducted on a continuous basis.

4. A process according to claim 3 which further comprises continuously recycling at least part of said first portion to the reactor.

5. A process according to claim 1 wherein (a) and (b) are conducted on a continuous basis and wherein the separation of (b) is effected by continuous flashing or distillation.

6. A process according to claim 1 wherein the hydrocarbylaluminum is trimethylaluminum and the aluminoxane is methylaluminoxane.

7. A process of forming methylaluminoxane which comprises:

(a) continuously feeding trimethylaluminum, water, and organic solvent to a reactor under temperature conditions and in proportions that form a solution containing a total in the range of about 0.5 to about 8 wt % of aluminum as dissolved hydrocarbylaluminum and methylaluminoxane species, and wherein for each mole part of aluminum in the solution there is in the solution in the range of about 0.10 to about 0.63 mole part of trimethylaluminum; (b) continuously degassing the reaction solution formed in (a);

(c) continuously flashing the degassed solution to form an overhead consisting essentially of about 0.5 to about 8 wt % of aluminum as trimethylaluminum dissolved in organic solvent, and bottoms consisting essentially of about 4 to about 20 wt % of aluminum as methylaluminoxane and trimethylaluminum, and wherein for each mole part of aluminum in solution in said bottoms, there is in the range of no more than about 0.03 to about 0.3 mole part of trimethylaluminum; and (d) recycling as a portion of the feed in (a), at least a portion of the overhead of (c).

8. A process according to claim 7 wherein makeup trimethylaluminum and makeup inert solvent are included in the feed in (a).

9. A process according to claim 8 wherein trimethylaluminum and inert solvent of the feed of (a) are made up of the recycle from (d) and said makeup trimethylaluminum and said makeup inert solvent.

10. A process according to claim 9 wherein the makeup trimethylaluminum is combined with the recycle from (d) before being fed in (a).

11. A process according to claim 9 wherein the makeup trimethylaluminum and a portion of the makeup inert solvent are combined with the recycle from (d) before being fed in (a).

12. A process according to claim 9 wherein the water and a portion of the inert solvent of the feed of (a) are mixed together before being fed in (a).

13. A process according to claim 9 wherein the makeup trimethylaluminum and a portion of the makeup inert solvent are combined with the recycle from (d) before being fed in (a), and wherein the water and another makeup portion of the inert solvent of the feed of (a) are mixed together before being fed in (a).

14. A process according to claim 7 wherein the solvent consists essentially of one or a mixture of inert hydrocarbons.

15. A process according to claim 7 wherein the solvent consists essentially of toluene.

16. A process according to claim 7 wherein the reactor is a loop reactor.

17. A process according to claim 7 wherein in (d) essentially the entire overhead of (c) is continuously recycled to form a part of the feed of (a).

18. A process according to claim 7 wherein the solvent consists essentially of one or a mixture of liquid inert hydrocarbons that has a boiling point or range below about 250° C.; wherein the bottoms of (c) are fed to the top of a countercurrent stripper column and wherein one or a mixture of inert hydrocarbons that has a boiling point or range below about 250° C. is fed into the bottom of said stripper column such that the stripper column yields (i) an overhead consisting essentially of trimethylaluminum and one or a mixture of inert hydrocarbons that has a boiling point or range below about 250° C., and (ii) bottoms consisting essentially of methylaluminoxane, trimethylaluminum and one or a mixture of inert hydrocarbons that has a boiling point or range below about 250° C., and wherein the overhead from said stripper column, and the overhead of (c) are recycled in (d) to form a part of the feed of (a).

19. A process according to claim 18 wherein the reactor is a loop reactor.

20. A process according to claim 19 wherein said one or a mixture of inert hydrocarbons in both cases is essentially entirely composed of toluene.

21. A process according to claim 7 wherein the solvent consists essentially of one or a mixture of inert hydrocarbons that has a boiling point or range below 250° C.; wherein the bottoms of (c) are fed to a wiped film evaporator to separate the bottoms into (i) an overhead consisting essentially of trimethylaluminum and one or a mixture of inert hydrocarbons that has a boiling point or range below 250° C., and (ii) bottoms consisting essentially of methylaluminoxane, trimethylaluminum and one or a mixture of inert hydrocarbons that has a boiling point or range below 250° C.; and wherein the overhead from said wiped film evaporator, and the overhead of (c) are recycled in (d) to form a part of the feed of (a).

22. A process according to claim 21 wherein the reactor is a loop reactor.

23. A process according to claim 22 wherein said one or a mixture of inert hydrocarbons in both cases is essentially entirely composed of toluene.

24. A process according to claim 7 wherein said temperature conditions and proportions in (a) are such that for each mole part of aluminum in said solution of (a) there is in said solution of (a) in the range of about 0.16 to about 0.63 mole part of trimethylaluminum; and wherein for each mole part of aluminum in solution in the bottoms from the continuous flashing in (c), said solution contains in the range of no more than about 0.05 to about 0.20 mole part of trimethylaluminum.

25. A process of forming methylaluminoxane which comprises:

(a) continuously feeding trimethylaluminum, water, and organic solvent to a reactor under temperature conditions and in proportions that form a solution containing a total in the range of about 0.5 to about 8 wt % of aluminum as (i) dissolved hydrocarbylaluminum and methylaluminoxane species, and (ii) finely-divided aluminum-containing solids, the aluminum content of said solids being not more than about 10% of the total weight of aluminum in (i) and (ii); and wherein for each mole part of dissolved aluminum in the solution, there is in the solution in the range of about 0.10 to about 0.63 mole part of trimethylaluminum;

(b) continuously degassing and removing said solids from the reaction solution formed in (a);

(c) continuously flashing the degassed, solids-free solution to form an overhead consisting essentially of about 0.5 to about 8 wt % of aluminum as trimethylaluminum dissolved in organic solvent, and bottoms consisting essentially of about 4 to about 20 wt % of aluminum as methylaluminoxane and trimethylaluminum, and wherein for each mole part of aluminum in solution in said bottoms, there is in the range of no more than about 0.03 to about 0.3 mole part of trimethylaluminum;

(d) recycling as a portion of the feed in (a), at least a portion of the overhead of (c).

26. A process according to claim 25 wherein said temperature conditions and proportions in (a) are such that for each mole part of aluminum in said solution of (a) there is in said solution of (a) in the range of about 0.16 to about 0.63 mole part of trimethylaluminum; and wherein for each mole part of aluminum in solution in the bottoms from the continuous flashing in (c), said solution contains in the range of no more than about 0.05 to about 0.20 mole part of trimethylaluminum.

27. A process according to claim 26 wherein the reactor is a continuous loop reactor, and wherein the inert solvent in (a) and (c) is one or a mixture of inert liquid hydrocarbons that has a boiling point or range below about 250° C.

* * * * *